United States Patent [19]

Pace

[11] Patent Number: 4,908,112

[45] Date of Patent: Mar. 13, 1990

[54] SILICON SEMICONDUCTOR WAFER FOR ANALYZING MICRONIC BIOLOGICAL SAMPLES

[75] Inventor: Salvatore J. Pace, Wilmington, Del.

[73] Assignee: E. I. Du Pont De Nemours & Co., Wilmington, Del.

[21] Appl. No.: 207,535

[22] Filed: Jun. 16, 1988

[51] Int. Cl.$^4$ .............................................. B01D 15/08
[52] U.S. Cl. ................................ 204/299 R; 356/344; 356/318; 250/461.2
[58] Field of Search ..................... 204/299 R; 356/344, 356/318; 250/461.2

[56] References Cited

U.S. PATENT DOCUMENTS

| | | | |
|---|---|---|---|
| 3,798,152 | 3/1974 | Cawley | 204/182.8 |
| 4,547,071 | 10/1985 | Teitelbaum | 356/344 |
| 4,652,757 | 3/1987 | Carver | 250/360.1 |
| 4,675,300 | 6/1987 | Zare | 356/318 |

FOREIGN PATENT DOCUMENTS

| | | |
|---|---|---|
| 0268406A | 5/1988 | European Pat. Off. . |
| 1458257 | 11/1966 | France .................. 204/182.8 |
| 2191110 | 12/1987 | United Kingdom . |

OTHER PUBLICATIONS

Jorgenson et al., "High Resolution Separations Based on Electrophresis and Electroosmosis", Journal of Chromatography, vol. 218, pp. 209 and 214, (1981).
Wallingford et al., "Capillary Zone Electrophoresis with Electrochemical Detection", Anal. Chem., vol. 59, pp. 1762-1766, (1987).
A. S. Cohen and L. B. Karger, Journal of Chromatography, vol. 397:409, (1987).
K. E. Petersen, Preceedings of IEEE, 70:420, (1982).
S. C. Terry, J. H. Jerman and J. B. Angell, IEEE Transactions of Electron Devices, ED-26, 1880, (1979).
D. L. Mould and R. L. M. Synge, Analyst, London 77, 964, (1952).
D. L. Mould and R. L. M. Synge, Biochem J., 58,571, (1954).
V. Pretorius, B. J. Hopkins and J. D. Shcieke, J. Chromatography, 99:23, (1974).
J. W. Jorgensen and K. D. LuKacs, Anal. Chem., 53:1298-1302, (1981).
J. W. Jorgensen and K. D. LuKas, J. Chromatography, 218:209-216, (1981).
A. S. Cohen, S. Terabe, J. A. Smith and B. L. Karger, Analytical Chemistry, vol. 59:1021, (1987).

*Primary Examiner*—John F. Niebling
*Assistant Examiner*—Isabelle Rodriguez

[57] ABSTRACT

An analytical separation device in which a capillary sized conduit is formed by a channel in a semiconductor device and the channel is closed by a glass plate. Electrodes are positioned in the channel and to activate the motion of liquids through the conduit by electroosmosis.

23 Claims, 8 Drawing Sheets

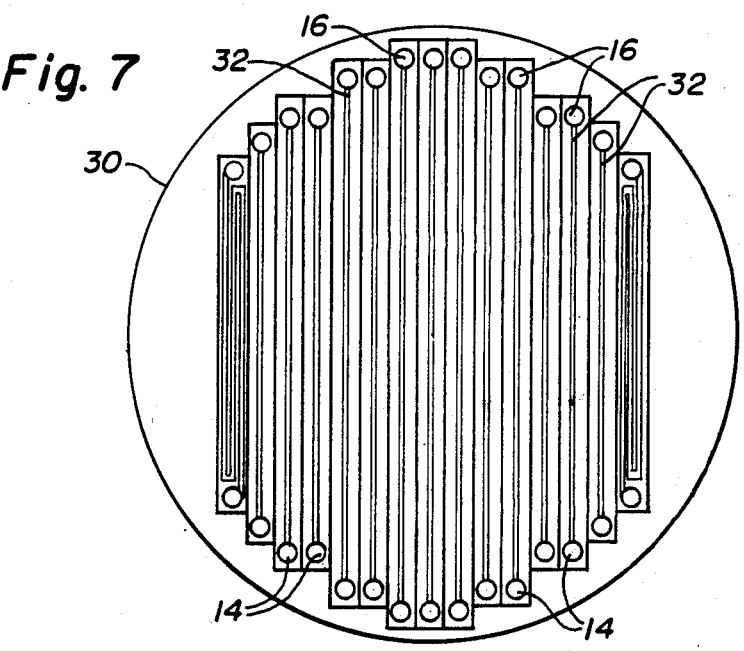
Fig. 7
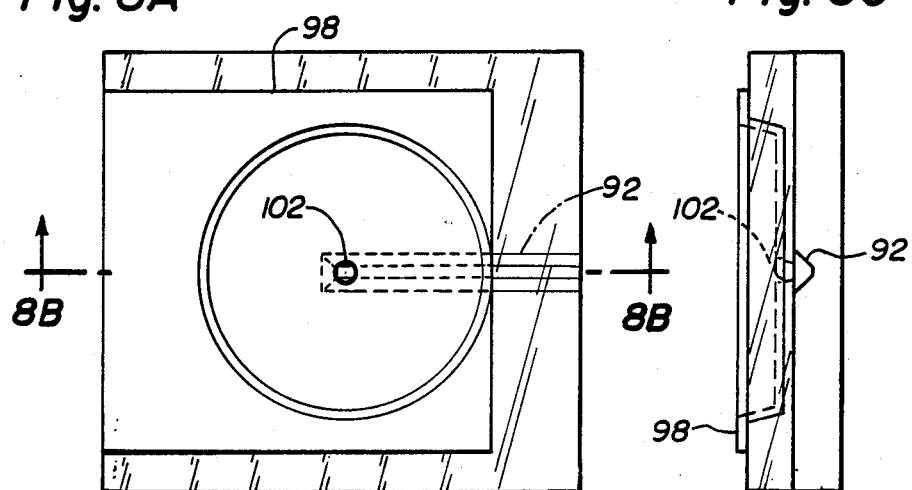
Fig. 8A
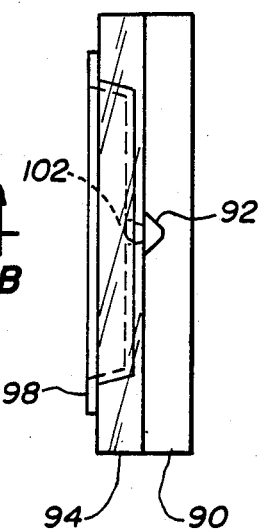
Fig. 8C
Fig. 8B

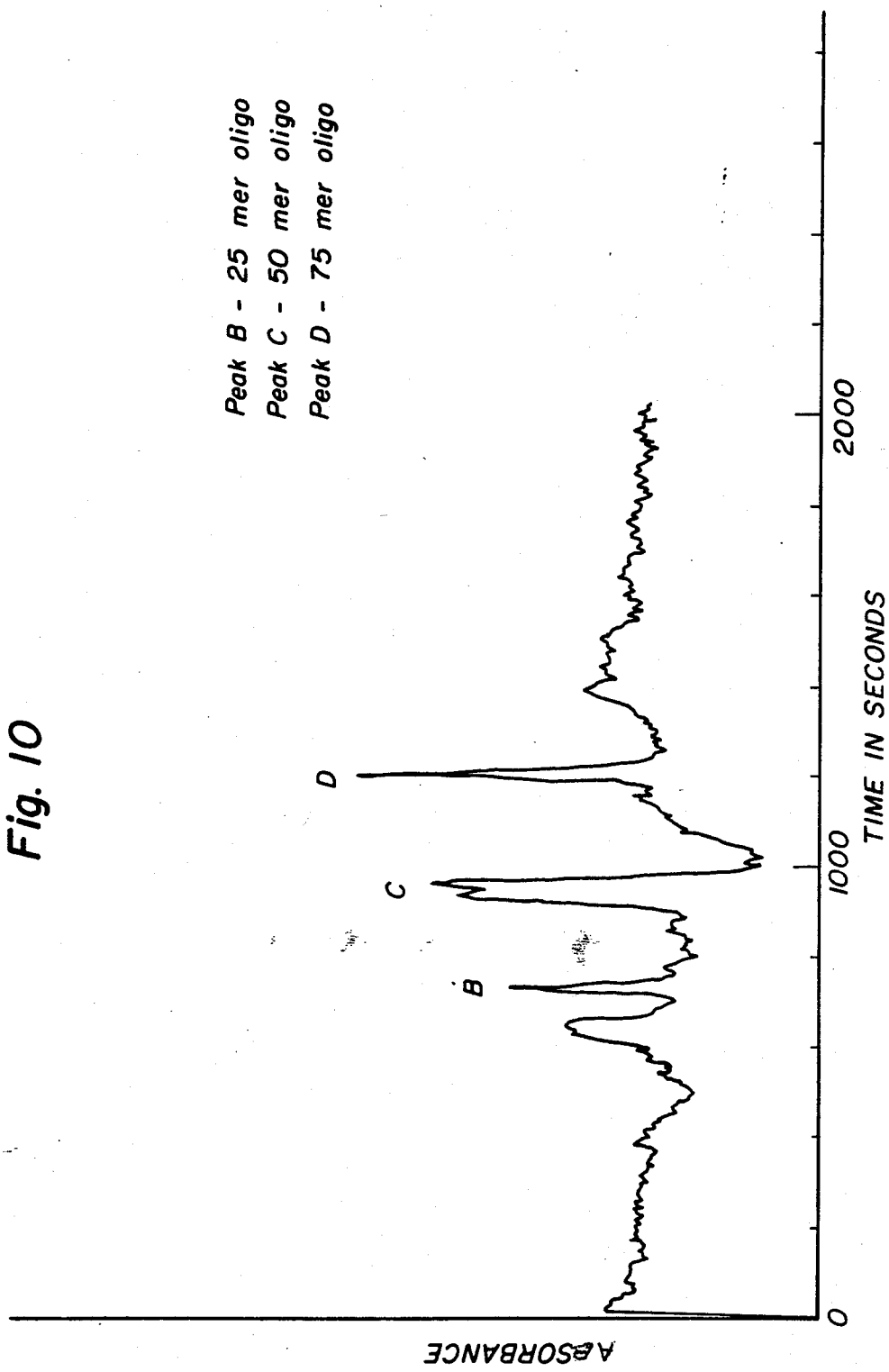

SILICON SEMICONDUCTOR WAFER FOR ANALYZING MICRONIC BIOLOGICAL SAMPLES

FIELD OF THE INVENTION

This invention relates to a method and device useful for the chromatographic and/or electrophoretic separation and detection of materials. Such separation is particularly useful in the analysis of biological molecules for research and diagnostic applications. In particular, the device and accompanying methods may be used to separate and detect microquantities of proteins and genetic material (RNA, DNA, etc.) using such principles of electrophoresis and chromatography in conduits of capillary and subcapillary dimensions.

1. BACKGROUND OF INVENTION

There exists a need for reliable, low-cost, automated analytical devices that allow facile and rapid separation and detection of microquantities of cellular tissue and genetic material for use in the research and diagnosis of disease. DNA analysis is an effective approach for the detection and identification of pathogenic microbes (i.e., viruses, bacteria, etc.) and is essential to the identification of genetic disorders. The ability to detect DNA with clinical specificity entails high resolution separation of RNA or DNA fragments, appropriate labeling chemistry for such fragments, and the adaption of high sensitivity sensors that are specific for the labeling chemistry employed. DNA probe technology is now an established tool of the molecular biologist for revealing the presence of diagnostically significant cells, whether they be diseased cells from the subject or infectious microorganisms.

Equally important to biomedical diagnosis is the ability to recognize minute variations in protein structure. For example, it has been reported that the detection of certain isoforms of the isoenzyme Creatine Kinase (CK-MB) is a marker for early detection of myocardial infarct. Similarly, proteins emanating from the core and envelope of viruses are used to detect early stages of viral infection (i.e., Auto immune disease syndrome AIDS).

On the biotechnology side, much of the success of modern molecular biology can be attributed to the development of reliable methods for the chemical structural analysis of nucleic acids. Determining the nucleotide sequence of DNA (deoxyribonucleic acid) and RNA (ribonucleic acid) is essential to recombinant DNA technology which aim is to alter the genes of microorganisms so as to ultimately produce human proteins (drugs) such as interferon, growth hormone, insulin, etc. In the plant world, DNA sequencing information is useful in developing plant strains that are resistant to adverse environmental conditions or disease. Without exception, analytical information is required at both the DNA level of information and also at the protein stage, to monitor gene expression during cloning.

2. Description of the Prior Art

Most prior art separations have been confined to relatively large channel dimensions (>50 micron diameter) dictated by the availability of fused silica capillaries. Electro-osmosis has been used to pump solvents in both thin layer and liquid chromatography [(D.L. Mould and R.L.M. Synge, *Analyst*, London, 77, 1952, 964), (D.L. Mould and R.L.M. Synge, *Biochem. J.*, 58, 1954, 571), (V. Pretorius, B.J. Hopkins and J.D. Schieke, *J. Chromatography*, 99, 1974, 23), (J.W. Jorgensen and K.D. LuKacs, *Anal. Chem.*, 53, 1981, 1298), and (J.W. Jorgensen and K.D. LuKacs, *J. Chromatography*, 218, 1981, 209). V. Pretorius, et al. used electroosmotic pumping for packed columns and open tubes and Jorgensen, et al. (*J. Chromatooraohv* Vol. 218, [1981] p. 209) for glass capillaries. Jorgensen also used electrophoresis to separate charged molecules in solutions pumped by electo-osmosis. A. S. Cohen, S. Terabe, J. A. Smith and B. L. Karger (Analytical Chemistry [1987], Vol. 59, p. 1021) utilized the interaction of solute and micelles to enhance the separation resolution of nucleotides. A. S. Cohen and L. B. Karger (Journal of Chromatography, Vol. 397, [1987] p. 409) demonstrated high resolution electrophoresis separation of proteins with polyacrylamide gel-filled fused silica capillaries.

The success of silicon in microelectronics is due to its unique properties as a structural material (K.E. Petersen, *Preceedings of IEEE*, 70, 1982, 420), as an electronic component, and as a chemical interface. A most noteworthy implementation of silicon as an integrated analytical component is the design of a gas chromatograph on a qilicon wafer [S.C. Terry, J.H. Jerman, and J.B. Angell, *IEEE Transactions on Electron Devices*, ED-26, (1979) 1880].

It is known in the art that fluids may be propelled through conduits by electro-osmotic force. Electroosmotic pressure is the consequence of charge build-up on the conduit surface. The buffer solution supplies the mobile counter ion to neutralize the surface charge and is the potential energy equivalent of the electroosmotic pressure. The application of an external voltage will cause a discharge via the mobile ions, resulting in an electro-kinetic current.

The discharge of ions causes the fluid in tne conduit to flow. The fluid flow is typically in the direction of the negative pole of the electric field since the counter ions are usually cations. The fluid flow direction is controlled by the magnitude of the applied voltage, its polarity, the surface charge, the channel dimensions and the viscosity of the medium. Unfortunately, the efforts in the prior art to utilize electro-osmotic pumping have been limited by the relatively large channel dimensions available in the glass capillaries used. Optimum flow velocity and control is achieved when the channel diameter is twice the ion double-layer thickness (i.e., $\sim 2\times 10^{-9}$ meter calculated for a 50 millimolar sodium phosphate solution). Furthermore, capillary electrophoresis as practiced by Jorgensen et al. requires very high voltages $\sim 25$ KVolts) to achieve significant flow velocities. The by-product of such high voltages is the formation of electrolysis products in the vicinity of the electrodes, and thus an unwanted side effect. The deployment of electrode implants within the silicon channels allows for the application of smaller voltages to achieve equivalent electric fields employed in capillary electrophoresis.

Capillary electrophoresis is practiced with fused silica capillaries with nominal dimensions of 1 meter length and 80–100 $\mu$m diameter. The voltage used to electro-osmotically drive the fluids through such capillaries at a rate of $\sim 0.2$ $\mu$l /minute is $\sim 25$ KV. In the practice of capillary electrophoresis, fluid flow is electro-osmotically driven toward a down-stream detector and the separation of sample components is accomplished electrophoretically (by charge), wall effects, or chemical interactions in the mobile phase.

Electroosmosis is mediated by surface charge, buffer electrolyte composition, viscosity of the fluid, channel or conduit diameter and the applied voltage. Best fluid control and optimum velocity is achieved when the capillary conduit diameter approaches twice the thickness of the Ion Double Layer Thickness. We estimate an ion double layer thickness for a 50 mM $Na_2H_2PO_4$ solution at approximately $10^{-9}$ meter vs the $10^4$ meter diameter of a capillary.

The major factors that limit separation performance by capillary electrophoresis are; diffusional zone spreading and dispersion of a zone by thermal convection. Dispersion due to thermal gradients can be controlled by the geometry of medium and the thermal conductivity and mass of the structural material that comprises the separation device. These same factors also limit resolution in gel-phase electrophoresis. Capillary electrophoresis is effective in separating proteins on the basis of charge/mass ratios. But, unlike gel-electrophoresis, capillary electrophoresis cannot separate on the basis of molecular size.

It is also known in the art that analytical performance is improved in capillary electrophoresis by reducing the capillary diameter. Similarly, gel-phase separations improve in resolution as the gel-thickness is reduced.

SUMMARY OF THE INVENTION

Many of the disadvantages of the prior art capillary type separation devices and methods are overcome by the device and methods of this invention. The device comprises a semiconductor wafer with micromachined conduits which conduits and reservoirs contain an electrode and detection electro-optics and/or electrochemical detectors. All analytical components needed for the separation and detection of the separated components are inclusive within the device and comprise sensing electrodes, drive electrodes, light guides, photodiodes and compartments for sample and reagent introduction.

According to the invention, an improved separation device, is constructed comprising a capillary sized, closed conduit adapted to be filled with liquid or solid materials for electrophoretic and/or chromatographic separations, means to introduce a sample to be processed into the conduit. The device is characterized by a semiconductor slab having a channel in one face and a cover plate attached to the one slab face to form the closed conduit, at least one interior dimension, transverse to the conduit being less than 100 $\mu$m, adapted to receive an ionizable liquid and means for applying an electric potential along the length of the interior of the conduit.

A method is described for electrophoretically separating a sample into components using a capillary sized conduit defined by an elongated channel in one face of a silicon slab, the channel being closed by a cover plate attached to the slab face, and comprises the steps of: introducing the sample into an ionic liquid; subjecting the liquid to a potential gradient along the conduit length; the silicon providing good heat dissipation characteristics which are enhanced by forming a channel with a high wall surface to volume ratio.

In another embodiment of the invention, an improved gel electrophoresis device with a first conduit having an inlet and an outlet is described, the conduit being filled with an electrophoretic gel, and the device includes means for applying an electric potential along the length of the interior of the conduit inlet, and a detector positioned along the conduit, the device characterized by all dimensions transverse to the conduit being greater than 100 $\mu$m, and the conduit being defined by a silica slab having a channel in one face and a cover plate attached to the one slab face to form the conduit. The benefits of the invention to such fields as molecular biology research and biomedical diagnostic testing are manifested as rapid, high resolution analysis of large, complex molecules requiring only minute sample size. The field of application ranges from DNA sequencing to diagnostic testing of genetic disease states and microbial infection.

Using the devices or methods of this invention, the analysis of DNA and/or proteins is accomplished with superior separation resolution and speed and with concomitantly minute sample size. Furthermore, sensitivity is also improved because of the integration of analytical components and electronics within a silicon structure that includes chemistry, fluidics, transducer and signal processing electronics. Silicon microelectronics technology allows the precise structuring of channels in the micrometer domain for the manipulation of minute sample volumes and the ability to integrate electro-optics components within such channels for improved signal/noise characteristics.

In accordance with another embodiment of the present invention, high resolution separation of oligonucleotides, DNA fragments and proteins is achieved in liquid-filled micro channels by applying the principles of capillary electrophoresis. An electric field is applied to narrow bore channels to effect both fluid flow and electrophoretic separation. The narrow channels provide efficient field flux concentration with minimal dispersion of migrating zones while also promoting nearly ideal plug flow dynamics. When wall coating are deployed, chromatographic interactions enhance the separation resolution of the migrating sample zone. The sample composition may include but is not limited to DNA, RNA, proteins, lipids, saccharides, and also intact cells such as viruses and bacteria.

It is the object of this invention to achieve superior DNA and proteins separation resolution in liquid channels by electrophoresis and chromatography. The focusing of electric fields within precisely machined grooves and the elimination of thermal zone dispersion are primary improvements.

Another object of this invention is to achieve high resolution separation of biological molecules in gel filled channels.

Yet another object of this invention is to achieve separations at high sample throughout rates and with minute sample size (<50 nanoliters).

A further object of this invention is to provide a means for actuating and controlling fluid flow at the very low volumes necessary for biological samples. Electro-osmotic pumping allows fluid flow control and EMF actuated sample injection.

Especially it is the object of this invention to provide a fully integrated diagnostic/analytical device that comprises: sample injection means, separation means, marking means, detection, and onboard electronics to effect signal processing and fluid movement.

BRIEF DESCRIPTION OF THE DRAWINGS

These and other objects, advantages and features of this invention will become apparent upon consideration of the following detailed description, taken in conjunction with the following drawings:

FIG. 7 is a plan view of plural channels formed in a single 100 mm diameter silicon wafer;

FIGS. 8A, 8B, and 8C are plan side view and end elevation view of the details of the reservoir construction used to provide an electrophoresis separation device using a silicon slab according to another embodiment of this invention;

FIG. 10 is a chromatographic representation of ten polynucleotides in which absorbed ultraviolet light is plotted as the ordinant and time as the absissa.

DETAILED DESCRIPTION OF THE INVENTION

According to this invention, capillary sized conduits are constructed from semiconductor materials using conduit dimensions in the 1 $\mu$m domain by fabrication methods generally applied by the semiconductor-microelectronics industry Conduit dimensions and geometries favorable for electro-osmotic fluid propulsion and electrophoretic and chromatographic separations may be structured on semiconductor and electrical insulator materials typically employed by the electronics industry. Such materials include glass, silicon, germanium and metal oxides. Especially appropriate are single crystal structural materials such as silicon because very precise features may be micromachined on the surface.

Silicon is a particularly suitable material because:
(1) Single crystal slab materials is obtainable in useful dimensions (i.e. 100 millimeter diameter, 500 $\mu$m thickness).
(2) It has a high thermal conductivity.
(3) It is harder than steel.
(4) It may be modified to an insulator or conductor.
(5) It naturally develops electro-osmotic pressure with aqueous electrolytes.
(6) Electronic and electro-optic components may be fabricated on it.

The preferred embodiment of this invention comprises: a channel <100 microns in diameter bounded by reservoirs (wells) etched onto a single crystal Si slab, implanted in such channel and wells are electrodes and the channel covered by a glass plate to allow the optical monitoring of migrating molecules in the conduit thus formed. An alternate embodiment comprises channel diameters >100 microns and filled with gels such as polyacrylamide to achieve high resolution separation of large molecules. The channel cross section is of trapezoidal geometry with the side walls defined by the <111> crystal plane of silicon subtended by an angle of 54.7° relative to the <100> crystal plane orientation. A laser beam is directed across the conduit for photon capture considerations and with optimal signal-to-noise characteristic. Other detectors may be adapted to the structure including: chemFET's, electrodes, electrochemiluminescence, mass spectrometry, optical fibers, wave guides, and piezoelectric sensors.

Figure 1:
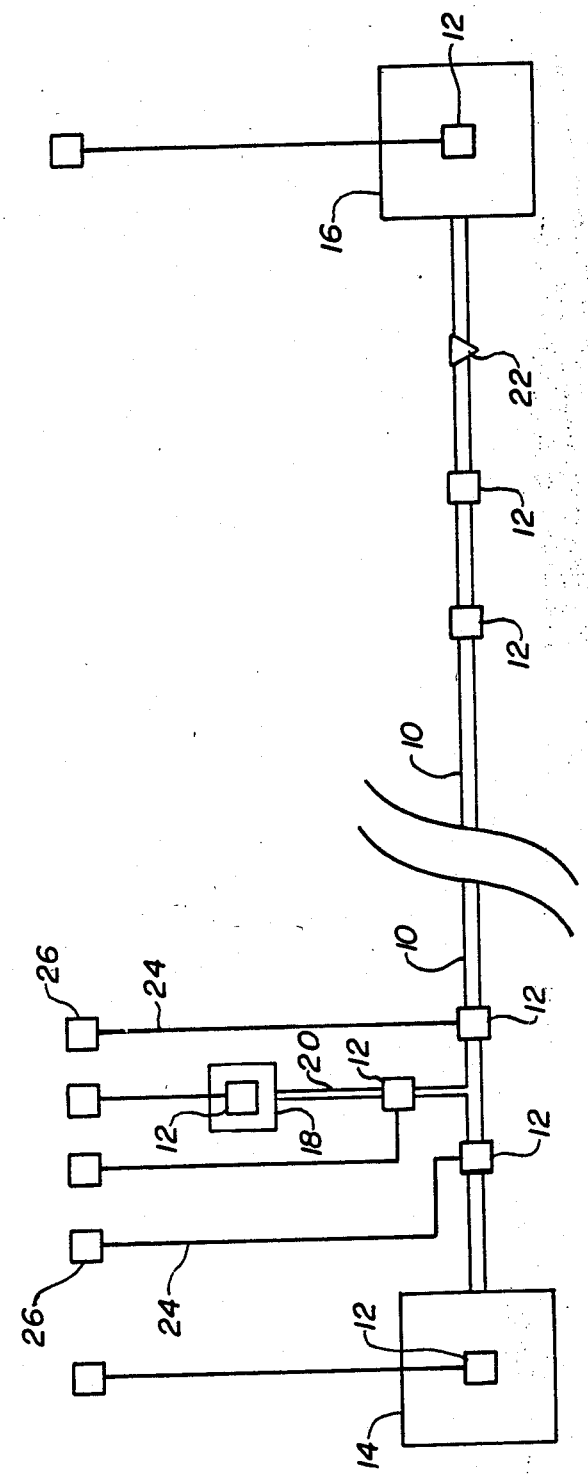
FIG. 1 is a schematic representation of a separation device constructed in accordance with a preferred embodiment of this invention.
Figure 2:
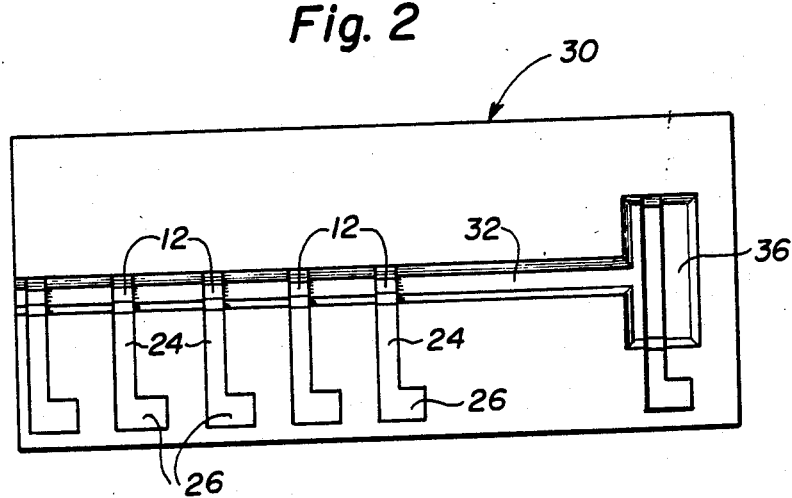
FIG. 2 is a fragmentary plan view of a separation device constructed in accordance with this invention utilizing a silicon slab.
Figure 3:
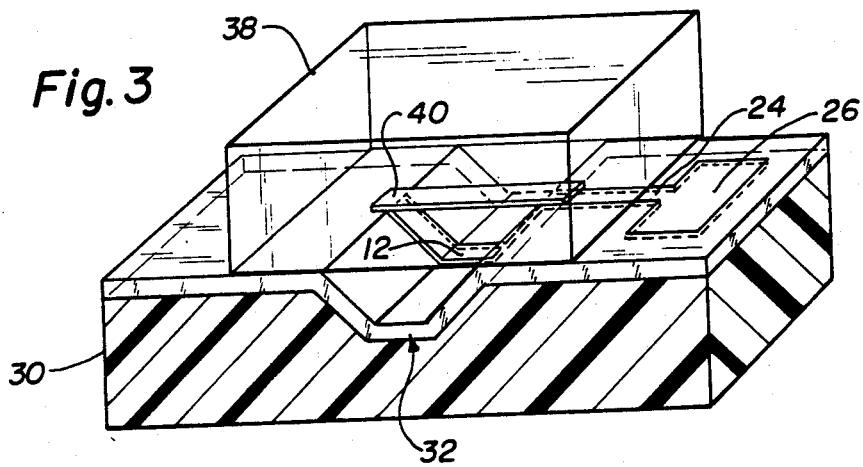
FIG. 3 is a cross-sectional view of a conduit constructed using the silicon slab of FIG. 2 together with a glass cover.

The structure of a preferred analytical device having a separation conduit is seen with reference to FIGS. 1, 2, 3, and 5. FIG. 1 is a schematic representation of the analytical device formed on a silicon slab comprising the essential functional components, i.e., a separation conduit 10, electrodes 12 formed in the conduit, a reservoir 14, and a recipient reservoir 16, a sample channel 18 and an injection conduit 20, and a detector 22. Each electrode 12 is connected through a conductor lead 24 to a bond pad 26, both being formed on the slab itself. A plan view of the device is depicted in FIG. 2 and a three-dimensional cross-section of the device is depicted in FIG. 3.

The analytical device is constructed by forming a channel or channels 32 in a silicon wafer or slab 30 typically a silicon slab 500 $\mu$m thick and 100 mm diameter yield channels that may be 80 ml long. These channels may follow, of course, a tortuous path if longer channels are desired, as may be seen by way of illustration in FIG. 7. Thus, a typical silicon slab 100 mm in diameter can provide several channels of varying lengths each with its own buffer reservoir 14 and recipient reservoir 16. The channel 32 is micromachined to have a trapezoidal cross-section. Preferably, the wall angle from the groove bottom plane is 54.7° and this angle (or wall pitch) is uniformly maintained through the entire channel length. The channel 32 as described is formed with a larger reservoir cavity 36 at either end which provide the buffer and recipient reservoirs 14 and 16 respectively (FIG. 1). A silicon dioxide ($SiO_2$) layer 32 is formed on the top of the silicon slab and in the channel. Electrodes 12 are implanted within the channel 32 and are connected to the bond pads 26 by respective conductor leads 24. Electrical connections to external instruments and power supplies may be attached to the bond pads. A glass cover plate made of pyrex glass 38 is secured to the top surface 32 of the slab 30 to provide a closed conduit to which the fluids may be directed described. The cover plate 38 typically may be 2 mm thick while the machine silicon slab 30 typically may be nominally taken from a circular slab 100 mm in diameter and 500 $\mu$m thick. The glass plate 38 is bonded to the oxide layer 32 and sealed at the top edge of the trapezoid to prevent liquid leaks that may shunt between several bond pads 26.

An auxiliary electrode 40 is formed on the underside of the glass plate 38 prior to securing it to the slab 30 such that each electrode 12 completely surrounds the formed conduit for maximal contact with the fluids therein. The auxiliary electrode 40 formed on the glass plate 38 may extend slightly beyond the dimension of the channel 32 so as to afford good contact with the conductor lead 32.

The bond pads 26, conductor leads 24, electrodes 12 and 40, are all formed as will be described by vapor depositing a conductor directly on the surface of either the silicon oxide or the glass as the case may be. Gold is preferred for this purpose although other conductors used in the semi-conductor industry such as tungsten, silver, copper, platinum, and the like. Preferably a polyimide gasket is used to bond the silicon to the glass plate and to prevent leakage beyond the confines of the channel, which together with the glass plate form the conduit.

The polyimide gasket is formed of material typically 8 μm thick and during bonding undergoes a sixty percent compression particularly in the region of the electrodes 12.

The electrodes 12 (and 40) are positioned at intervals along the length of the conduit as will be later described and also in each reservoir 14 and 16.

The channel 32 is formed using conventional micromachining techniques used in the electronics industry in connection with semi-conductor devices. In the preferred case at hand where the channel is formed in a silicon chip, the device depicted in FIGS. 1, 2, and 3 is formed by the following steps:

(1) Develop the desired channel and reservoir pattern by photolithography on a photo mask.
(2) Develop the etch protect mask pattern (by, $SiO_2$ or $Si_3N_4$) on a <100> oriented single crystal silicon wafer.
(3) Implant Boron (~$10^{20}$ atoms/cm$^3$) at a prescribed depth in the wafer as an etch stop.
(4) Anisotropically etch exposed silicon with ethylene diamine pyrocatechol (in water). A timed etch alternatively may be used instead of the etch stop.
(5) Thermally oxidize the top of the silicon to $SiO_2$ especially within the channel and reservoirs.
(6) Establish a desired mask pattern for the lead conductors, electrodes and bond pads using suitable photo tools.
(7) Vapor deposit gold Au° on the unmasked portions of the wafer to form the lead conductors, electrodes and bond pads. Other conductors may substitute for Au° (e.g. W, Ag, Cu, Pt, etc.).
(8) Etch or ultrosonically drill access holes in the glass cover plate.
(9) Place a polyimide "gasket" pattern onto the silicon surface. Polyimide is used to bond silicon to glass plate.
(10) Pressure bond glass cover plate to silicon slab. The polyimide gasket is positioned along the groove top edges to effect a liquid tight seal. A typical channel may be 10 μm wide at the bottom, 38 μm wide at the top, and 20 μm deep. Access holes (not shown) may be formed in the glass plate 38 over each reservoirs 14, 16, to permit filling in the buffer, as will be described, or sample 20.

Alternatively, steps 7 through 10 may be replaced by another fabrication route. The Au° lead conductor 24 may be formed by heavy doping of the silicon by boron to yield a $p^{30}$ (conductor) channel. The electrophoresis drive electrode may be formed by either overlaying the p+ termination within the channel by a layer of Au° or the p+ terminus itself can function as the electrode. Since the silicon surface is relatively flat (i.e., encumbered by the Au° lead pattern that is elevated above the Si surface by the Au° thickness). A "Mallory" bond seals the glass plate directly to the silicon slab. The Mallory bond is an electric field assisted glass - metal thermal sealing process of the P.R. Mallory Co. The bond is formed by thermally compressing at 400° C. the Si/glass assembly under ~ 1200 volts.

Alternate channel-geometries cross-sections such as rectangular, semicircular and V-shaped grooves may be created as follows:
(a) V-shaped channels are created by anisotropic etch of <100> silicon with no etch stop.
(b) Rectangular channels are created by anisotropic etching of <110> silicon.
(c) Semi-circular channels are created by isotropic etching with agitation of etchant solution/substrate.

The trapezoidal channels are preferred because they accommodate light absorbance detection measurements or more preferrably, a fluorescence detection scheme as shown in FIG. (5). This diagram assumes nominal channel dimensions of 38 μm at the top of the trapezoid, 10 μm at the bottom and 20 μm depth. An incident laser beam 40, 20 μm wide, can be comfortably positioned to penetrate the glass plate 38, reflect from one wall 42 of the channel, cross the channel width and reflect from the opposite wall 44 to pass back through the glass plate 38 and away from the device surface. In so doing, any reporter labeled molecules within the channel will fluoresce and the emitted radiation 46 is captured by a photodetector 48 via a lens 50. A suitable reporter labeling, less exciting and fluorescence detecting system is described in a published EPO patent application No. 02 52 683 published Jan. 13, 1988. An improved system is described in an article by Prober et al., Science, Vol. 238, page 336, Oct. 16, 1987 and in EPO patent application No. 071,060,874, issued May 23, 1989, as U.S. Pat. No. 4,833,332.

To increased channel length beyond the limitation of silicon wafer diameter, the longitudinal geometry of the groove can assume "serpentine" or coil patterns as seen in FIG. 7 these patterns can be built on devices prepared with either Mallory and polyimide glass-to-silicon bonds.

Figure 6:
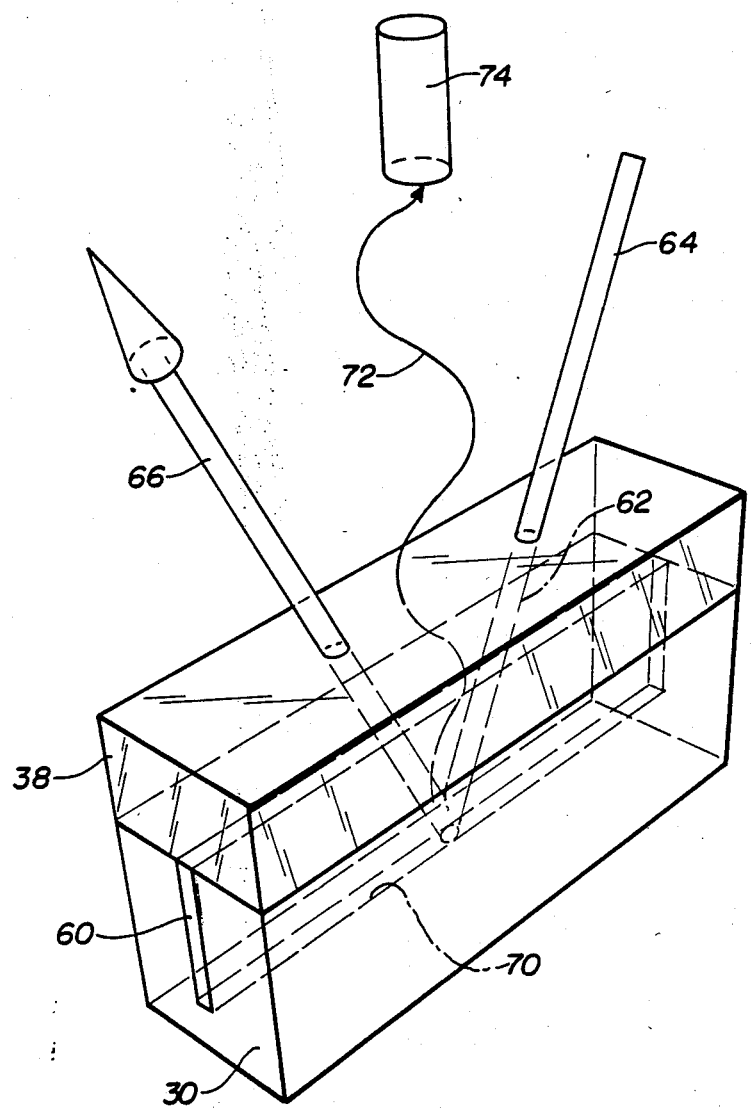
FIG. 6 is a pictorial representation of an alternative construction of the conduit in a silicon slab of this invention utilizing a laser photodetection system.

In an alternative embodiment of the invention optical fibers or light guides may be used to direct the laser beam through the channel. This alternative embodiment shown in FIG. 6 preferably uses a deep channel 60 having a rectangular cross section along its length and preferably a high aspect ration of 10:1 (height:width). This enhances heat exchange with the silicon which improves analytical performance. Optical fibers or light guides 64 and 66 are positioned above the glass cover plate, which using known techniques has a material density profile to focus light from the fibers and compensate for the refractive index, to guide the light beam directed through the fiber 64 will pass as depicted by the dotted lines 68 through the glass and the entire height of the conduit 60 be reflected from the bottom surface 70 through the glass plate and return fiber 66 to a suitable detector. Alternatively, radiation emitted from fluorescing material passing through the channel is depicted by the line 72 and may be detected by a suitable photo-detector 74 as hereinbefore described. The deep channel pattern also improves the optical direction sensitivity by increasing the optical path length while maintaining small channel dimensions. Alternative detectors may be incorporated in the channel geometry or adapted for use with the device. These detectors include Chem FET's, electrochemiluminescence, mass spectrometers, waveguides and pregoelectric sensors.

Returning now to FIGS. 1-3, the method of use of the analytical device is now described. The reservoirs 14 and 16 are first filled with buffer solution by injecting the fluid into buffer reservoir 14 via an access hole (not shown) through the glass plate 38. Capillary action typically fills the conduits 10 and 20 within seconds. Sample is injected via a syringe through a hole (not shown) in the glass plate 38 into sample chamber 26. Sample is then introduced into separation channel 20 by electro-osmotic pumping, i.e., by applying a voltage between the electrodes in the sample reservoir 18 and one of the downstream electrodes 12 (preferably electrode 70 which is closest to the injection conduits intersection with the separation conduit. Excess sample is returned into sample reservoir 26 by reverse polarity voltage applied to the sample reservoir electrode and the electrode 72 upstream from the intersections. The sample zone may be focused by establishing an EMF between the buffer and recipient reservoirs electrodes to move through the separation conduit past the detector 22. The detector signal is then recorded as a function of time, reflecting the movement of molecules through the conduit 10 and specifically the detector 22.

Figure 4:
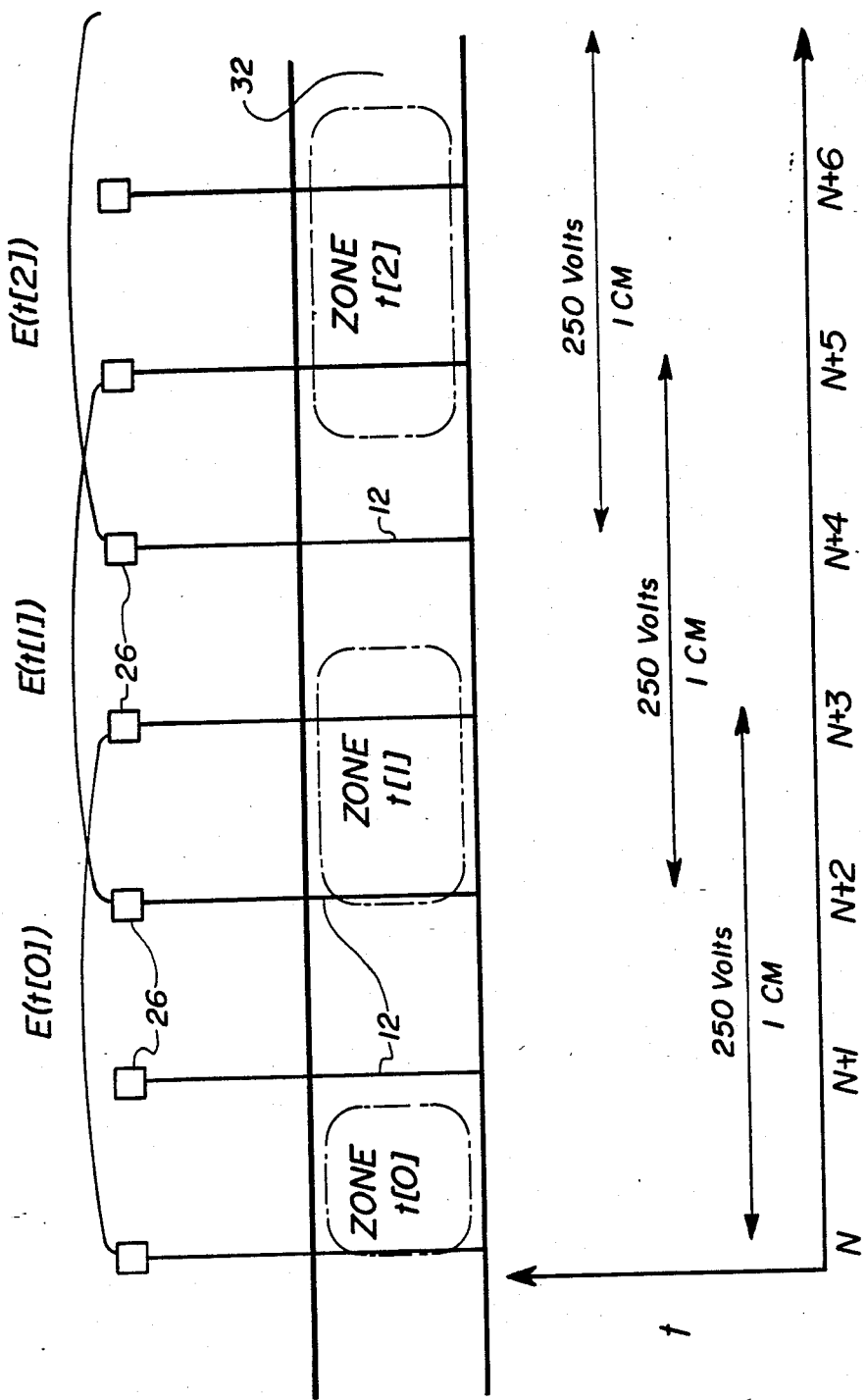
FIG. 4 is a schematic time representation of the manner in which the flow of liquids through the conduit of this invention is maintained.

To achieve high resolution separation by molecular charge requires the application of intense electric field gradients, of the order of 250 volts/cm. Rather than apply a large voltage along the entire length of the conduit, much smaller voltages may be applied between more closely spaced but staggered electrodes 122 as seen in FIG. 4 and yet maintain high intensity fields. Such a voltage program scheme that applies small voltages across staggered electrode pairs that straddle the sample zone as it migrates down stream. The timing sequence for the application of voltages follows the down-stream motion of the sample zone and the spacing between electrode pairs is at least twice the zone width at the channel end. In so doing the problem of electrolyte/solution break-down due to electrolysis and gas generation is avoided. In the simplest case, a voltage may be applied between the electrodes in the buffer and recipient chambers to drive the electrophoresis.

Another embodiment of this invention is shown in FIGS. 7 and 8A, 8B, and 8C. In this embodiment a plurality of conduits are constructed as previously described, but in this case are all constructed on a single semi-conductor wafer. The conduits are all formed to accept gel electrophoresis media and thus the conduit diameters are typically provided to be >100 $\mu$m. In this case reservoirs 14 and 16 are formed in either end of the respective channels 32 which form the conduits. In this case fifteen parallel channels, ranging typically in length from 56 mm to 135 mm, are illustrated. Two of the channels are in the form of "serpentine" longitudinal geometry and thus are of greater length. In this instance, however, the reservoirs are not formed in the semi-conductor wafer, but rather are formed in the pyrex glass which covers the open channels and the wafer to form the conduits. Thus, it is seen more clearly in FIGS. 8A–8C. The silicon wafer 90 is formed as previously described to have a channel 92 with an $SiO_2$ upper surface. It also includes a pyrex glass plate 94 which has an etched reservoir 96. The reservoir is left open to the atmosphere. An electrode 98 is formed on the surface of the reservoir and extends over to a bond pad 100. In this case the entire bottom of the reservoir is formed with the electrode 98. A hole 102 is formed in the bottom over the channel 92 so as to provide access thereto. The hole passes through both the electrode and the glass 94. In a typical case the reservoir 96, which is illustrated as circular, may be 3.2 mm in diameter with a fill capacity of 3 $\mu$m. In this case for electrophoretic application the channel 92 may have a width of 380 $\mu$m at the top, 100 $\mu$m at the bottom, with a depth of 200 $\mu$m. These dimensions allow a wider diameter laser beam than that previously described and hence a higher detection sensitivity, but with somewhat lower separation resolution.

This device as noted above is specifically designed to be used with gel media for electrophoresis separation. The method of use is as follows: The groove is first filled with gel preparation fluid (e.g. monomer and cross-linker of any suitable gel such as polyacrylamide gels). The liquid is injected into reservoir 96 and the channel fills by capillary action up to the reservoir 96. The gel typically sets within a few minutes. The reservoirs are filled with an appropriate buffer. Sample is then injected by a gas-chromatography type syringe (nominally 50 nanolites) into the buffer filled reservoir 96 and the electrophoreses run, subsequently, by applying a voltage to electrodes 98 between reservoirs at each end of each conduit.

The invention employs a semiconductor microanalytical device and uses principles of electrophoresis and chromatography to achieve separation performance superior to that of the prior art on minute biological samples. Electro-osmosis, electrophoresis and chromatography can be practiced on silicon micromachined structures in a synergistic manner. Electro-osmotic fluid flow actuation is best controlled when the channel dimensions approach the electrical double layer thickness, which for all practical purposes is accomplished with channel dimensions of <100 microns diameter. Couple to the above the ability to integrate electronic components in the conduit and the device of the invention is an analytical instrument and method that can function in the microdimensional environment to transport fluids and separate their content.

Several analytical functions become possible:
(a) The movement of nanoliter fluid volumes by proper application of electromotive force (EMF).
(b) Electric field gates (or valves) to control passage of fluids and/or particles.
(c) The routing of fluids through conduits by voltage actuation of electrode implants within such conduits.
(d) Chromatographic separation of molecules by wall interactions.
(e) Integration of the detector within the device itself.
(f) All functions of an analytical instrument may be integrated within a single Si wafer: Sample injection, separation, reagent introduction, detection, signal conditioning circuitry, logic and on-board intelligence.
(g) The high resolution electrophoresis separation of molecules in liquid and/or gel media.

EXAMPLE 1

(Demonstration of Principle-Capillary electrophoresis)

Figure 9:
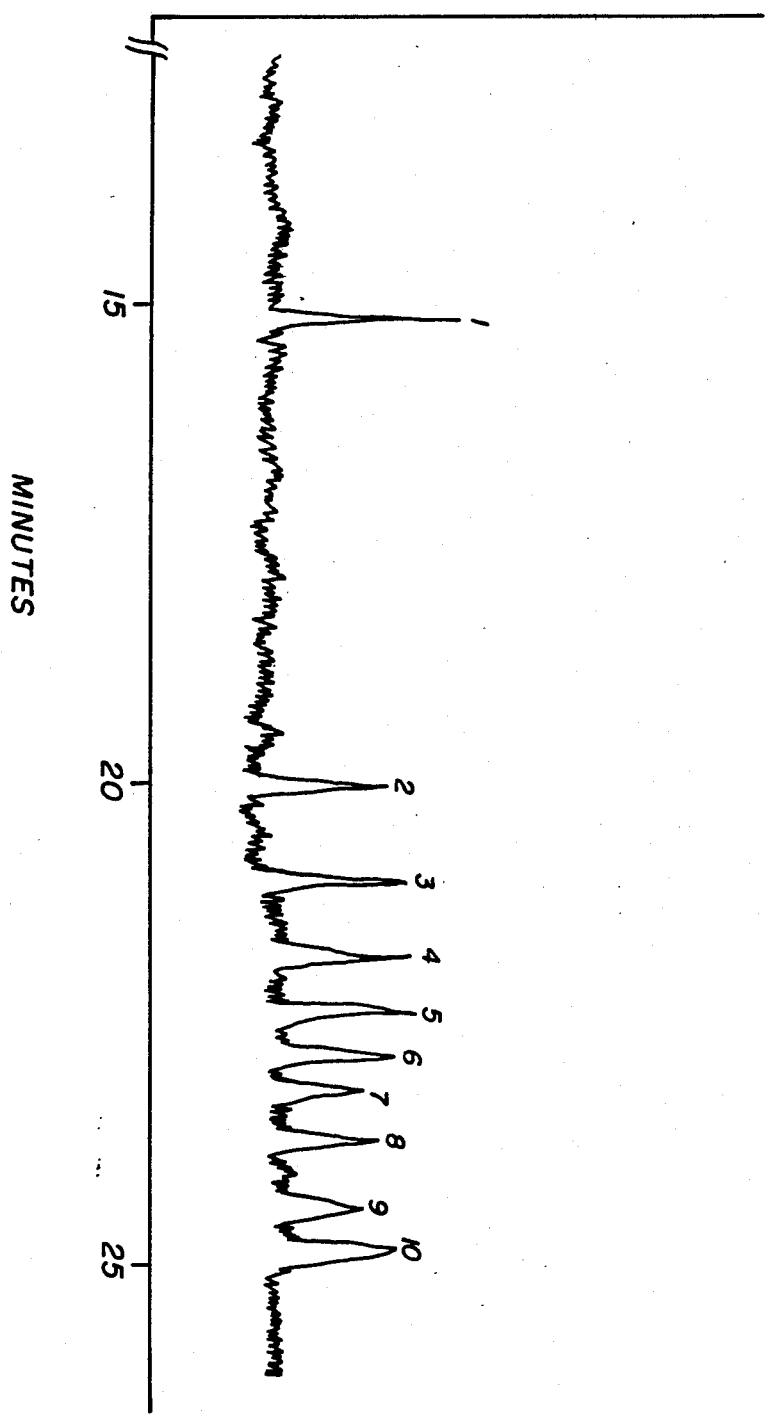
FIG. 9 is a chromatogram in which emitted light is plotted as the ordinant and time as the absissa depicting the separation of all of the nucleotides.

A capillary electrophoresis experiment run on a polynucleotide mixture comprising polyadenosines of various polymer lengths from 2-mer to 20-mer is shown on FIG. 9. This experiment was run on a fused silica tube, 50 microns in diameter and 60 cm length. 25 KV was applied as the separation voltage and the sample injection was accomplished by a 5 sec. pulse at 5 KV. The oligonucleotides were detected by UV absorbance at 254 nm as they migrate past the detector window as a function of time. This experiment is an indication of the resolving power based solely on molecular charge differentiation.

The test polynucleotide sample consists of polyadenosine fragments of varying lengths, as opposed to oligonucleotides that comprise random sequences of different nucleotides (e.g., adenosine, cytosine, guanosine, and tyrosine). The fragment composition is as follows and corresponds to the Peak Nos. as labeled on FIG. (5):

| Peak # | Component | Theor. Plates |
|---|---|---|
| 1 | pb(A)2 | 131,777 |
| 2 | pb(A)5 | 183,186 |
| 3 | pb(A)6 | 141,859 |
| 4 | pb(A)7 | 206,989 |
| 5 | pb(A)8 | 181,468 |
| 6 | pb(A)9 | 144,499 |
| 7 | pb(A)10 | 133,510 |
| 8 | pb(A)12 | 147,295 |
| 9 | pb(A)16 | 183,322 |
| 10 | pb(A)20 | 119,785 |

The sample was injected into the capillary by dipping the input capillary orifice into a sample cup containing the polyadenosine fragments and applying 5 KV for 5 seconds to a Pt electrode in the sample cup. Although the actual sample volume was not measured precisely, it represents approximately 0.001 of the total fill volume of the capillary (2 μL). The separation of the fragments is completed in 25 minutes. The separation is accomplished electrophoretically due to the difference in charge between fragments, although the major motion is electo-osmotic flow in the downstream direction toward the detector.

EXAMPLE 2

Fluorimetric Detection of DNA

Double stranded DNA may be detected fluorimetrically by labeling the DNA fragments with intercolating dyes. This experiment utilized an HP-1046A detector, adapted to a 107 μm fused silica capillary and the DNA was labelled with 4,6-diamidine-2-phenylindole-HCl (DAPI). All other capillary electrophoresis conditions are the same as those given in Example I. The detector was adjusted to an excitation wavelength of Ex=366 μm, and an emission wavelength Em=460μm. The dsDNA test sample comprises of Lambda-DNA-Hind III/Phi-X-174 RF, DNA-Hiinc II Digest. The electrophoresis separation was run in a liquid 0.05 M phosphate buffer of pH 7.0. The fragments separate into three major bands which are further resolved. The peaks observed correlate well with an agarose gel-electrophoresis control, run for the equivalent sample.

Dye Reagent

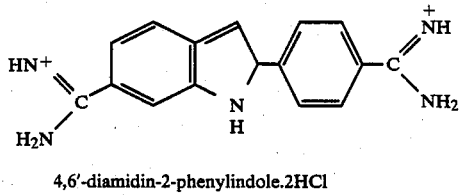

4,6'-diamidin-2-phenylindole.2HCl
(DAPI)

EXAMPLE 3

Electrophoresis Separation in Gel-Filled Channels

Figure 5:
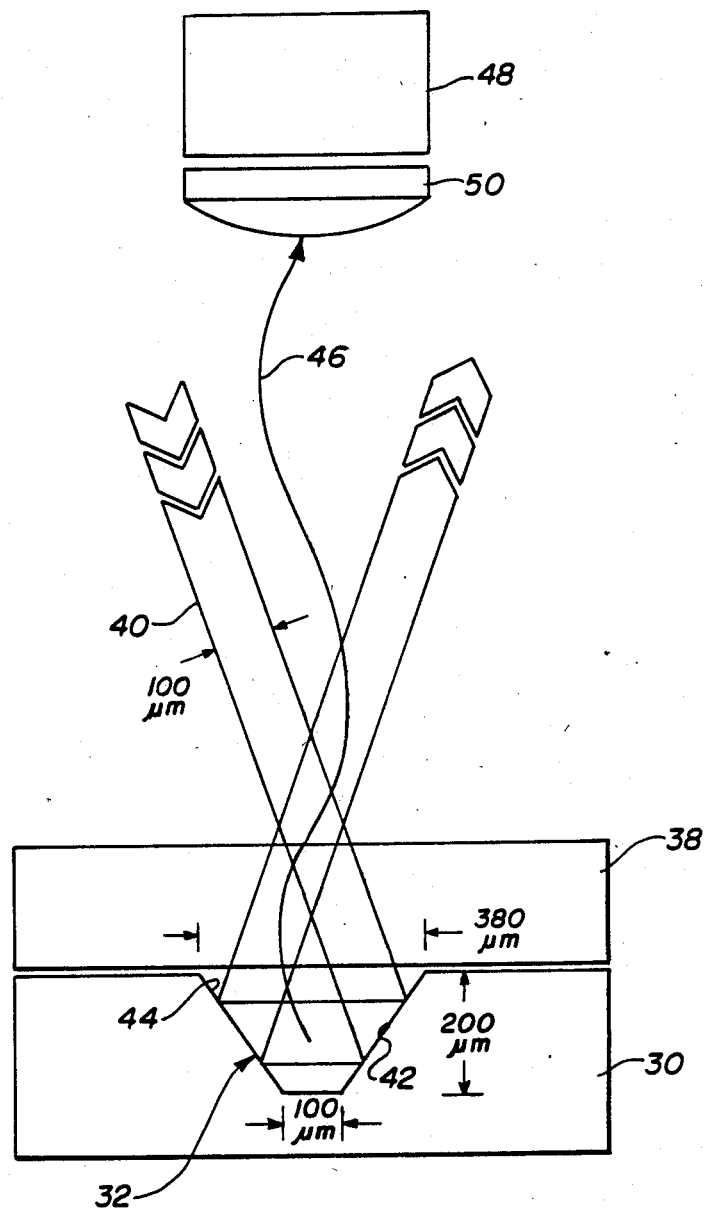
FIG. 5 is a diagrammatic representation of the manner in which a laser detector is used in conjunction with the conduit and silicon slab of this invention.

This experiment was performed with the the device described in FIGS. 8A–C, coupled to the laser fluorimetric detection system described in FIG. 5. The channels were filled with 6% polyacrylanide gel in pH 8.3 Tris-hydroxymethylamine methane buffer. The sample comprises a three component mixture of synthesized oligonucleotides. The oligonucleotides are a random sequence of the essential nucleotides of DNA and the single stranded chain in 5'-end labelled with a fluorophore dye (T'-phosphoramidite):

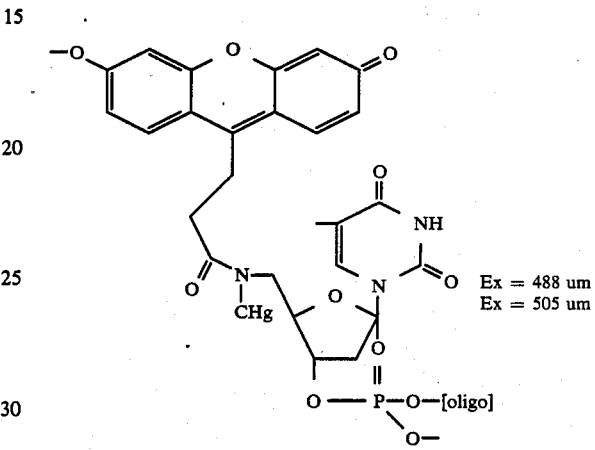

Ex = 488 um
Ex = 505 um

The resulting electropherogram is shown in FIG. 10. The actual dye-labeled chain lengths comprising the sample are 25-mer, 50-mer and 75-mer molecular size. The excitation wavelength of the laser was 488 μm and the photomultiplier emission wavelength was set to 505 μm. Peaks B, C, and D correspond to the 25, 50 and 75-mer oligos, respectively, and peak X is unreacted fluorophore-labeled thymidine, a synthetic impurity of one of the oligomer preparations.

One notes the speed of migration and the separation resolution achieved with a 6 cm long channel. No sample zone pre-concentration was used nor any attempt made to enhance the detection sensitivity by electro-optic manipulation or signal conditioning. The actual sample size injected by GC syringe was 40 nanoliters which translates to $3 \times 10^{-15}$ moles of 25-mer oligonucleotide detected.

I claim:

1. An improved separation device, comprising a capillary sized, closed conduit adapted to be filled with liquid or solid materials for electrophoretic and/or chromatographic separations, means to introduce a sample to be processed into the conduit, the device characterized by
a semiconductor slab having a channel in one face and a cover plate attached to the one slab to form the closed conduit, adapted to receive an ionizable liquid, and means for applying an electric potential along the length of the interior of the conduit.

2. The device set forth in claim 1 further characterized by the conduit being rectangular, ellipsoidal, triangular, or trapezoidal in cross-section, the slab being silicon, and the plate being glass, at least one interior dimension transverse to the conduit being less than 100 μ.

3. The device set forth in claim 1 further characterized by the conduit having a rectangular cross-section with height and width dimensions, the height to width aspect ratio of the conduit being greater than 10:1.

4. The device set forth in claim 2 wherein the means for applying a potential comprises at least one electrode disposed in the channel on the slab and at least one electrode disposed in a reservoir.

5. The device set forth in claim 4 further characterized by the slab and cover plate defining a reservoir at each end of the channel.

6. The device set forth in claim 4 further characterized by the slab and cover plate defining a second conduit intersecting with the first conduit.

7. The device set forth in claim 6 further characterized by a detector associated with the conduit adapted to detect any sample passing through the conduit, the detector having a laser and a photo detector, the laser beam being directed transversely of and through the interior of the conduit, the photodetector positioned to view the conduit.

8. The device set forth in claim 2 wherein the means for applying a potential comprises at least one electrode disposed in the channel on the slab and at least one electrode disposed in one reservoir, and means to vary the electrical potential of each such electrode to control the flow of the ionizable liquid by electroosmosis.

9. The device set forth in claim 8 further characterized by the slab and cover plate defining a second conduit intersecting with the first conduit.

10. The device set forth in claim 9 further characterized by a detector positioned to recognize particles of interest in ionizable liquid of at least one point in the conduit, the detector having a laser and a photo detector, the laser beam being directed transversely of and through the interior of the conduit.

11. The device set forth in claim 3 wherein the means for applying a potential comprises at least one electrode disposed in the channel on the slab and at least one electrode disposed in a reservoir, and means to vary the electrical potential of each such electrode to control he electroosmatic flow of the ionizable liquid by electroosmosis.

12. The device set forth in claim 11 further characterized by the slab and cover plate defining a second conduit intersecting with the first conduit.

13. The device set forth in claim 12 further characterized by a detector associated with the conduit adapted to detect the ionizable liquid exiting the conduit, the detector having a laser and a photo detector, the laser beam being directed transversely of and through the interior of the conduit.

14. The device set forth in claim 2 further characterized by a detector associated with the conduit to detect the ionizable liquid exiting the conduit, the detector having a laser and a photo detector, the laser beam being directed transversely of said through the interior of the conduit, the photo detector positioned to view the conduit.

15. The device set forth in claim 1 further characterized by the depth to width aspect ratio of the interior of the conduit is greater than 1.

16. An improved gel electrophoresis device with a first conduit having an inlet and an outlet, the conduit being filled with an electrophoretic gel, means for applying an electric potential along the length of the interior of the conduit inlet, and a detector positioned along the conduit, the device characterized by all dimensions transverse to the conduit being greater than 100 $\mu$m, and the conduit being defined by a silicon slab having a channel in one face and a cover plate attached to the one slab face to form the conduit.

17. The device set forth in claim 16 further characterized by the means for applying a potential comprising at least one electrode in the channel of the slab and at least one electrode in a reservoir, and means to adjust independently the electrical potential of each electrode to control the migration rate of the electrically charged sample molecules.

18. The device set forth in claim 16 wherein the sample includes a fluorescing dye and the device is further characterized by the detector being positioned to recognize particles of interest in a sample at least one point in the conduit, the detector having a laser and a photo detector, the laser beam being directed transversely through the interior of the conduit to provide such energy that will cause excitation of the fluorescing dye molecules attached to the electrically charged molecules.

19. The device set forth in claim 17 further characterized by the conduit being trapezoidal in cross-section, with the sides of the trapezoid forming 54.7° exterior angles with the base, the laser beam being directed through the plate to one side to be reflected through the conduit and back out of the conduit by the second side and the plate to the photo detector.

20. The device set forth in claim 16 wherein the sample includes a fluorescing dye and the device is further characterized by a detector system being positioned to recognize particles of interest in a sample at least one point in the conduit, the detector having a laser and a photo detector, the laser beam being directed transversely through the interior of the conduit to provide such energy that will cause excitation of the fluorescing dye molecules attached to the electrically charged molecules.

21. The device set forth in claim 16 further characterized by the means for applying a potential comprising at least one electrode disposed in the channel of the slab and at least one electrode in a reservoir, and means to adjust independently the electrical potential of each electrode to control the migration rate of the electrically charged sample molecules.

22. The device set forth in claim 18 further characterized by the means to introduce a sample comprises a second channel formed by the slab and plate defining an inlet conduit connected to the first conduit, the inlet conduit having electrodes disposed therein in the channel, and means to vary the electrical potential of each electrode to direct the sample from the inlet conduit to the first conduit.

23. The device set forth in claim 16 further characterized by the means to introduce a sample comprises a second channel formed by the slab and plate defining an inlet conduit connected to the first conduit, the inlet conduit having electrodes disposed therein in the channel, and means to vary the electrical potential of each electrode to direct the sample from the inlet conduit to the first conduit.

* * * * *